United States Patent [19]

Ellis

[11] Patent Number: 4,665,951

[45] Date of Patent: May 19, 1987

[54] PROSTHETIC LIGAMENT

[76] Inventor: Julian G. Ellis, 18 Tavistock Avenue, Mapperly Park, Nottingham NG3 5BD, United Kingdom

[21] Appl. No.: 710,033

[22] Filed: Mar. 11, 1985

[51] Int. Cl.⁴ .......................... A61F 1/00; D03D 3/02
[52] U.S. Cl. .................................. 139/387 R; 623/13
[58] Field of Search ................... 139/388, 384, 387 R; 623/13

[56] References Cited

U.S. PATENT DOCUMENTS

| | | | |
|---|---|---|---|
| 3,095,017 | 6/1963 | Bleiler et al. | 139/387 R |
| 3,130,418 | 4/1964 | Head et al. | 139/387 R |
| 3,973,277 | 8/1976 | Semple et al. | 623/13 |
| 4,149,277 | 4/1979 | Bokros | 623/13 |
| 4,255,820 | 3/1981 | Rothermel et al. | 623/13 |
| 4,340,091 | 7/1982 | Skelton et al. | 139/387 R |
| 4,585,485 | 4/1986 | Kurland | 623/13 |

FOREIGN PATENT DOCUMENTS 126520  11/1984  European Pat. Off. .
2836921  3/1980  Fed. Rep. of Germany .
1526762  9/1978  United Kingdom .

Primary Examiner—Henry S. Jaudon
Attorney, Agent, or Firm—Handal & Morofsky

[57] ABSTRACT

A prosthetic ligament comprises an elongate woven fabric member having two ends, including a portion woven in the form of a tube, a tail section extending between the tubular portion and a first end, the tail section having a tubular configuration with a single longitudinal opening, a pocket extending from the tubular portion towards the second end of the member and having a tubular configuration with a single longitudinal opening, and a tightly woven portion extending from the pocket towards said second end wherein the member comprises a unitary woven structure.

Weaving of the prosthesis as a unitary structure avoids the need for any subsequent sewing. The structure is also stronger and does not have a selvedge which could cause irritation.

9 Claims, 5 Drawing Figures

ENDS

ENDS

Key:
■ Face end lifting on face pick
· Face end lifting on back pick
○ Back end lifting on back pick

PROSTHETIC LIGAMENT

BACKGROUND OF THE INVENTION

This invention relates generally to prosthetic devices and specifically to an artificial skeletal ligament.

A ligament is a band of tough tissue which serves to connect the articular extremities of bones or to support an organ. Skeletal ligaments flexibly stabilise joints and consequently must be able to withstand considerable forces. Ligaments are often damaged by being subjected to excessive forces. Ligaments rarely mend completely and the working of the damaged joint may be permanently impaired.

Surgical repair of a torn ligament is often difficult and unsatisfactory not only because a long period of convalescence is required but also because the repaired joint may move in directions which are not normally allowed causing pain in the joint and undue wear to the skeletal members.

Various artificial ligaments have been proposed for replacement of damaged natural ligaments.

United Kingdom Pat. No. 1526762 (Richards Manufacturing Company) disclosed a prosthetic ligament comprising an elongate flexible portion with enlarged head at each end, the head serving to secure the flexible portion in bores through the skeletal member in which the ligament is attached.

U.S. Pat. No. 3,973,277 (Semple et al) disclosed a similar arrangement in which the flexible portion is secured in bores in the skeletal members by means of tapered porous plugs. German Offenlegungschrift No. 2836921 (Sigri Elektrographit GmbH) discloses use of a textile strip secured at each end to a skeletal member. A woven prosthesis may have apertures of varying sizes, as disclosed in U.S. Pat. No. 4,255,820 to control ingrowth of tissue.

European Patent Application No. 126520 (Seedhom, Ellis & Fujikawa) discloses a woven fabric prosthesis ligament having the form of a tube, one end of which has two slits on opposite sides of the tube. The end of the tube adjacent the slits is sealed by stitching to form a pocket to receive a bone plug during installation of the prosthesis. The opposite end of the tube has an elongate slit, open at the end to receive a second bone plug. The tubular structure is formed by stitching a flat ribbon of woven fabric.

Stitching of the prosthesis does not remove the selvedge which may cause irritation and may be a source of structural weakness. In addition stitching requires a separate manufacturing step after weaving the ribbon.

It is an object of this invention to provide a prosthetic ligament which does not incorporate stitching or other separate means of fastening the woven portions.

A prosthetic ligament in accordance with this invention comprises an elongate woven fabric member having two ends, including a portion woven in the form of a tube, a tail section extending between the tubular portion and a first end, the tail section having a tubular configuration with a single longitudinal opening, a pocket extending from the tubular portion towards the second end of the member and having a tubular configuration with a single longitudinal opening, and a tightly woven portion extending from the pocket towards said second end, wherein the member comprises a unitary woven structure.

Weaving of the prosthesis as a unitary structure avoids the need for any subsequent sewing. The structure is also stronger and does not have a selvedge which could cause irritation.

The prosthesis is preferably woven in a leno or mock leno weave having apertures adapted to receive ingrowth of tissue. Preferred embodiments of the invention incorporate 10 to 50 apertures per $cm^2$, more preferably 15 to 36 apertures per $cm^2$. A uniform distribution of apertures is preferred. The prosthesis may be composed of fibres sold under the Trade Marks 'Terylene' or 'Dacron' or other polyester compounds although alternative artificial or natural fibres may be employed.

A cord or thread may be attached to the second end to facilitate threading of the prosthesis through the skeletal members.

In use of the prosthesis, bone plugs are removed from the skeletal members forming apertures which partially penetrate each skeletal member. Smaller diameter bores are then made through the skeletal members from the bottoms of the apertures. The prosthesis is threaded through the apertures using the cord and a bone plug located in the pocket. The prosthesis is then pulled so that the bone plug is relocated in the aperture, securing the prosthesis in the first skeletal member. The second bone plug may then be placed in the tail portion and reinserted in the respective aperture and sutured to secure the other end of the prosthesis.

BRIEF DESCRIPTION OF THE DRAWINGS

The invention is further described by means of example and not in any limitative sense, with reference to the accompanying drawings, of which.

DESCRIPTION OF THE PREFERRED EMBODIMENTS

Figure 1:
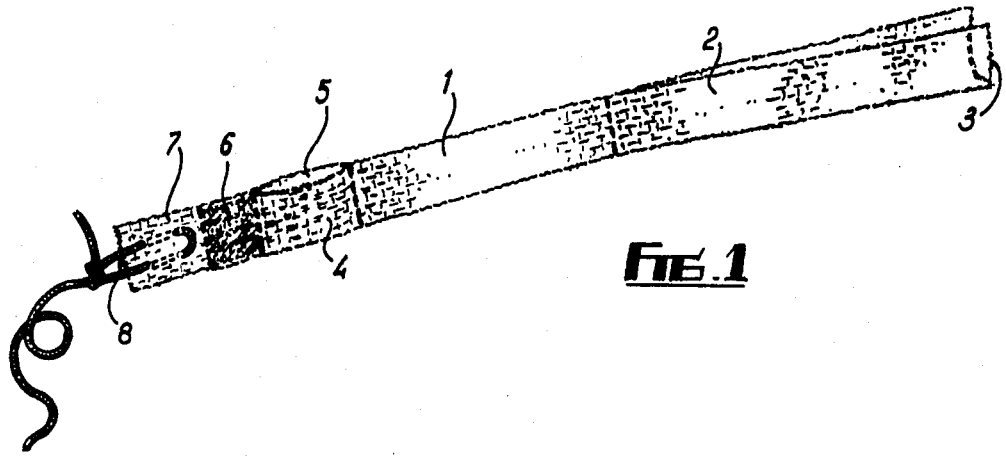
FIG. 1 shows a prosthesis in accordance with this invention.

FIG. 1 shows a prosthetic ligament, constructed in accordance with this invention, comprising an elongate member woven from a polyester fibre such as those marketed under the Trade Marks Dacron or Terylene.

A tubular portion 1 is disposed between the ends 3,8 of the member. A tail 2 extends from the tubular portion 1 to a first end 3. The tail has the shape of the tubular portion but has a longitudinal opening extending from the tubular portion to the end 3. The tail 2 may be opened to form a flat ribbon. A pocket is disposed between a second end 8 and the tubular portion, adjacent the tubular portion. The pocket comprises a woven section 4 having a longitudinal opening 5 in a similar manner to the tail. A single opening 5 is preferred to facilitate retention of a bone plug therein. A tightly woven portion 6 extends adjacent the pockets 4,5 towards the second end 8. The tightly woven portion is woven as a plain weave or twill to withstand the strain imposed on the ligament in use. A terminal portion 7 is woven in the form of a tube although any other convenient configuration may be used. The terminal portion 7 serves to retain a cord 8 used to draw the prosthesis through the bones in the skeletal members during installation.

The member is woven as a single, integral structure, the warp threads running continuously the full length of the member. A single continuous weft thread is preferably used.

FIGS. 2 to 5 show weaving plans.

The warp yarns are set out across the width of the reed in groups forming repeating sequences of twelve groups.

Figure 2:
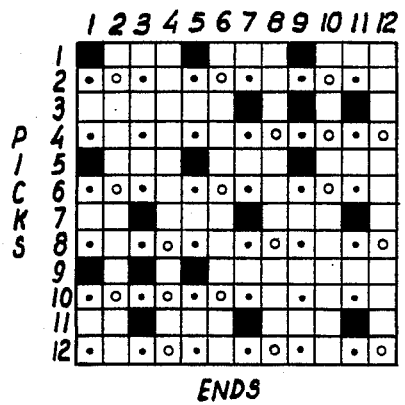
FIG. 2 is a weaving plan for the tubular section of the prosthesis.

FIG. 2 shows a mock leno weaving plan for the face and back parts of the tubular section 1 viewed from above, the warps extending between the top and bottom edges of the plan. Each square represents a pick, each horizontal row of picks being a single weft insertion. Warp ends which form the top of the fabric alternate with warp ends which form the bottom of the fabric. Alternate horizontal rows show the weft passing on the face and back parts of the tube; the shaded squares each representing a face end lifting on the face pick, the dotted squares each representing a face end lifting on the back pick and the squares containing circles each representing a back end lifting on the back pick. The weft passes in a continuous, generally spiral manner between picks on the upper and lower parts of the tube. For convenience the ends across of each repeating sequence are referred to as ends 1 and 12, and the picks are labelled picks 1 to 12.

Pick One:

For the first insertion of the weft forming the tubular section, warp ends 1,5 and 9 are lifted to form the front of the tube.

Pick Two:

For the second insertion warp ends which form the front of the fabric 1,3,5,7,9 and 11 are lifted with ends 2,6 and 10 from those ends which form part of the back portion of the tube.

Pick Three:

Warp ends 7,9 and 11 are lifted, again to form the front of the tube.

Pick Four:

The front warp ends 1,3,5,7,9 and 11 are lifted together with warp ends 8,10 and 12 from the ends forming the back of the fabric.

Pick Five:

Warp ends 1,5 and 9 are lifted.

Pick Six:

Front ends 1,3,5,7,9 and 11 are lifted together with back ends 2,6 and 10.

Pick Seven:

Front warp ends 3,7 and 11 are lifted.

Pick Eight:

Warp ends 1,3,5,7,9,11 from the front of the tube and ends 4,8 and 12 from the back are lifted.

Pick Nine:

Ends 1,3 and 5 from the front of the tube are lifted

Pick Ten:

Ends 1,3,5,7,9 and 11 from the front and ends 2,4 and 6 from the back are lifted.

Pick Eleven:

Ends 3,7 and 11 are lifted.

Pick Twelve:

Ends 1,3,5,7,9 and 11 from the front and 4,8 and 12 from the ends that form the back of the fabric are lifted. This sequence of lifting is repeated for the number of times required to form the desired length of tube. The sequence is than altered when the pocket and tube parts are woven.

Figure 3:
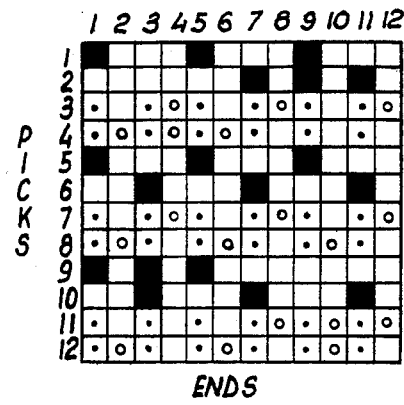
FIG. 3 is a weaving plan for the pocket and tail sections of the prosthesis.
Figure 4:
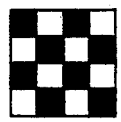
FIG. 4 is a partial weaving plan for the tightly woven section of the prosthesis.
Figure 5:
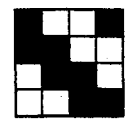
FIG. 5 is a partial alternative weaving plan for the tubular portion of the prosthesis.

FIG. 3 shows the mock leno weaving plan for the face and back parts of the tail and pocket section. The symbols used have the same meaning as in FIG. 1.

The ends and picks of the weave of the pocket and tail portions are raised or lowered only when the weft is on one side of the fabric, no change from the face to back sections taking place while the shuttle or weft inserter is on the other side of the fabric. This results in the fabric having a longitudinal opening.

The sequence of weaving is such that two picks are inserted to form the front of the fabric, followed by another two picks to form the back of the tube. This lifting sequence is such that a complete weaving pattern repeat for forming a pocket or tail is completed in a cycle of every 12 picks.

Pick One: Ends 1,5 and 9 are lifted

Pick Two: Ends 7,9 and 11 are lifted

Pick Three:(Forming the back of the fabric) front ends 1,3,5,7,9 and 11 and back ends 4,8 and 12 are lifted Pick Four: Front ends 1,3,5,7,9 and 11, with back ends 2,4 and 6 are lifted Pick Five: Ends 1,5 and 9 are lifted to form a front portion Pick Six: Ends 3,7 and 11 are lifted Pick Seven: Front ends 1,3,5,7,9 and 11 and back ends 4,8 and 12 are lifted Pick Eight: Ends 1,3,5,7,9 and 11, and back ends 2,6 and 10 are lifted Pick Nine: Front ends 1,3 and 5 are lifted Pick Ten: Front ends 3,7 and 11 are lifted Pick Eleven: All front ends, i.e. 1,3,5,7,9 and 11 and back ends 8,10 and 12 are lifted Pick Twelve: Ends 1,3,5,7,9 and 11 and back ends 2, 6 and 10 are lifted This sequence is repeated the required number of times.

There are three warp threads or groups of threads in each dent. During the weaving process the first and last threads lift alike and the middle thread lifts in such a manner as to allow the outside threads to come together. In the next dent the outside threads are lifted exactly oppositely to the outside threads of the first dent. Thus they are kept away from the threads in the adjacent dent.

The picks are also arranged in threes, thereby creating the apertures in the fabric which are necessary for tissue ingrowth.

Alternative mock leno cloth constructions may be employed for the tubular or tail portions. For example if the third and ninth ends of FIG. 2 are lifted at the third and ninth picks respectively i.e. at alternate picks, the centre thread in each group of three is woven between each weft, resulting in a superior scissoring of the warps between the ends. This may produce a more stable fabric.

A leno weave may be used in place of a mock leno weave. In this case the warp ends cross over each other to give the scissoring effect required to produce an open fabric. However it would be extremely rare to have access to a loom capable of the long pattern repeat which is necessary for the fabric of the present invention, together with the special heald arrangement necessary for a leno weave.

It may also be possible to manufacture the prosthesis using a loom having two fabrics simultaneously, for example as is done in the manufacture of velvet. In this process the two fabrics would be joined at their edges rather than across their entire surfaces. However, the selvedge which would necessarily be formed would be untidy and may snag e.g. on bony spicules during the surgical operation.

What I claim is:

1. A prosthetic ligament comprising an elongate woven fabric member having two ends, including a portion woven in the form of a tube, a tail section extending between the tubular portion and a first end, the tail section having a tubular configuration with a single longitudinal opening, a pocket extending from the tubular portion towards the second end of the member and having a tubular configuration with a single longitudinal opening, and a tightly woven portion extending from the pocket towards said second end, wherein the member comprises a unitary woven structure.

2. A prosthetic ligament as claimed in claim 1, wherein the tubular pocket and tail portions are woven in a mock leno weave.

3. A prosthetic ligament as claimed in claim 1, wherein the tubular, pocket and tail portions are woven in a leno weave.

4. A prosthetic ligament as claimed in claim 1, wherein the weft yarn of the tubular portion is disposed in a spiral configuration.

5. A method of weaving a prosthetic ligament of the type which comprises an elongate woven fabric member having two ends, including a portion woven in the form of a tube, a tail section extending between the tubular portion and a first end, the tail section having a tubular configuration with a single longitudinal opening, a pocket extending from the tubular portion towards the second end of the member and having a tubular configuration with a single longitudinal opening, and a tightly woven portion extending from the pocket towards said second end, the member comprising a unitary woven structure, wherein the tubular, tail and pocket portions of the ligament are woven on face and back sections having two sides and wherein during weaving of the tail and pocket portions the weft passes between the face and back sections only at one side of the weave.

6. A method of weaving a prosthetic ligament as claimed in claim 5, wherein the warp yarns are arranged in groups, the groups being arranged to form one or more repeating sequences of twelve groups and wherein the groups of warp yarns are woven with groups of one or more weft yarns and wherein the groups of weft yarns of the tubular portion of the ligament are woven by repeatedly forming a sequence of warp sheds between respective weft insertions, the sequence of sheds being formed by the steps of:
1. lifting the first, fifth and ninth group of warp ends;
2. lifting the first, second, third, fifth, sixth, seventh, ninth, tenth and eleventh group of warp ends;
3. lifting the seventh, ninth and eleventh groups of warp ends;
4. lifting the first, third, fifth, seventh, eighth, ninth, tenth, eleventh and twelfth group of warp ends;
5. lifting the first, fifth and ninth groups of warp ends;
6. lifting the first, second, third, fifth, sixth, seventh, ninth, tenth and eleventh groups of warp ends:
7. lifting the third, seventh and eleventh groups of warp ends;
8. lifting the first, third, fourth, fifth, seventh, eighth, ninth, eleventh and twelfth groups of warp ends;
9. lifting the first, third and fifth groups of warp ends
10. lifting the first, second, third, fourth, fifth, sixth, seventh, ninth and eleventh groups of warp ends.
11. lifting the third, seventh and eleventh groups of warp ends;
12. lifting the first, third, fourth, fifth, seventh, eighth, ninth, eleventh and twelfth groups of warp ends.

7. A method of weaving a prosthetic ligament as claimed in claim 5, wherein the warp yarns are arranged in groups, the groups being arranged to form one or more repeating sequences of twelve groups and wherein the groups of warp yarns are woven with groups of one or more weft yarns and wherein the groups of weft yarns of the pocket and tail portions of the ligament are woven by repeatedly forming a sequence of warp sheds between respective weft insertions, the sequence of sheds being formed by the steps of:
1. lifting the first, fifth and ninth groups of warp ends;
2. lifting the seventh, ninth and eleventh groups of warp ends;
3. lifting the first, third, fourth, fifth, seventh, eighth, ninth, eleventh and twelfth groups of warp ends;
4. lifting the first, second, third, fourth, fifth, sixth, seventh, ninth and eleventh groups of warp ends;
5. lifting the first, fifth and ninth groups of warp ends;
6. lifting the third, seventh and eleventh groups of warp ends;
7. lifting the first, third, fourth, fifth, seventh, eighth, ninth, eleventh and twelfth groups of warp ends;
8. lifting the first, second, third, sixth, seventh, ninth, tenth, and eleventh groups of warp ends;
9. lifting the first, third and fifth groups of warp ends;
10. lifting the third, seventh and eleventh groups of warp ends;
11. lifting the first, third, fifth, seventh, eighth, ninth, tenth, eleventh and twelfth groups of warp ends;
12. lifting the first, second, third, fifth, sixth, seventh, ninth, tenth and eleventh groups of warp ends.

8. A method of weaving a prosthetic ligament as in claim 5, wherein the tubular portion is woven according to the weaving plan:
On the first pick: for the first insertion of the weft forming the tubular section, lifting warp ends 1, 5 and 9 to form the front of the tube;
On the second pick: for the second insertion lifting warp ends which form the front of the fabric 1, 3, 5, 7, 9 and 11 with ends 2, 6 and 10 from those ends which form part of the back portion of the tube;
On the third pick: lifting warp ends 7, 9 and 11, again to form the front of the tube;
On the fourth pick: lifting the front warp ends 1, 3, 5, 7, 9 and 11 together with warp ends 8, 10 and 12 from the ends forming the back of the fabric;
On the fifth pick: lifting warp ends 1, 5 and 9;
On the sixth pick: lifting front ends 1, 3, 5, 7, 9 and 11 together with back ends 2, 6 and 10;
On the seventh pick: lifting warp ends 3, 7 and 11;
On the eighth pick: lifting warp ends 1, 3, 5, 7, 9 and 11 from the front of the tube and ends 4, 8 and 12 from the back;
On the ninth pick: lifting ends 1, 3 and 5 from the front of the tube;
On the tenth pick: lifting ends 1, 3, 5, 7, 9 and 11 from the front and ends 2, 4 and 6 from the back;
On the eleventh pick: lifting ends 3, 7 and 11;
On the twelfth pick: lifting ends 1, 3, 5, 7, 9 and 11 from the front and 4, 8 and 12 from the ends that form the back of the fabric.

9. A method of weaving a prosthetic ligament as claimed in claim 5, wherein the pocket and tail portion are woven according to the weaving plan:
- On the first pick: lifting ends 1, 5 and 9;
- On the second pick: lifting ends 7, 9 and 11;
- On the third pick: lifting front ends 1, 3, 5, 7, 9 and 11 and back ends 4, 8 and 12 to form the back of the fabric;
- On the fourth pick: lifting front ends 1, 3, 5, 7, 9 and 11, with back ends 2, 4 and 6;
- On the fifth pick: lifting ends 1, 5 and 9 to form a front portion;
- On the sixth pick: lifting ends 3, 7 and 11;
- On the seventh pick: lifting front ends 1, 3, 5, 7, 9 and 11, and back ends 4, 8 and 12;
- On the eighth pick: lifting ends 1, 3, 5, 7, 9 and 11, and back ends 2, 6 and 10;
- On the ninth pick: lifting front ends 1, 3 and 5;
- On the tenth pick: lifting front ends 3, 7 and 11;
- On the eleventh pick: lifting all front ends, that is, 1, 3, 5, 7, 9 and 11 and back ends 8, 10 and 12;
- On the twelfth pick: lifting ends 1, 3, 5, 7, 9 and 11 and back ends 2 , 6 and 10.

* * * * *